(12) United States Patent
Beyer et al.

(10) Patent No.: US 8,152,860 B2
(45) Date of Patent: Apr. 10, 2012

(54) COSMETIC COMPOSITION FOR COLORING HAIR COMPRISING A DIRECT HAIR DYE AND A CARRIER SYSTEM COMPRISING POLYSACCHARIDES

(75) Inventors: Monika Beyer, Nidderau-Ostheim (DE); Dirk Teichmüller, Linsengericht (DE)

(73) Assignee: ROVI Cosmetics International GmbH, Schluchtern (DE)

( * ) Notice: Subject to any disclaimer, the term of this patent is extended or adjusted under 35 U.S.C. 154(b) by 0 days.

(21) Appl. No.: 13/156,412

(22) Filed: Jun. 9, 2011

(65) Prior Publication Data

US 2011/0302725 A1    Dec. 15, 2011

(30) Foreign Application Priority Data

Jun. 11, 2010    (DE) .......................... 10 2010 030 000

(51) Int. Cl.
*A61Q 5/10*    (2006.01)
(52) U.S. Cl. .............. 8/405; 8/426; 8/455; 8/463; 8/526
(58) Field of Classification Search .............. 8/405, 426, 8/455, 463, 526
See application file for complete search history.

(56) References Cited

U.S. PATENT DOCUMENTS 7,670,391 B2 *    3/2010    Schmenger et al. .............. 8/405

2008/0279805 A1    11/2008    Giroud

FOREIGN PATENT DOCUMENTS

DE    10 2004 028 465    6/2004
WO    01/62376    8/2001

OTHER PUBLICATIONS

German Examination Report issued Feb. 4, 2011 in German Patent Application No. 10 2010 030 000.4.

* cited by examiner

*Primary Examiner* — Eisa Elhilo
(74) *Attorney, Agent, or Firm* — Drinker Biddle & Reath LLP

(57) ABSTRACT

The present invention concerns cosmetic compositions for coloring hair comprising at least one direct hair dye and a carrier system for the at least one direct hair dye, and the use of such compositions in cosmetic formulations for coloring hair. To provide a possible way with which the permanence of the bond of direct hair dyes to the hair can be improved, with the aim of direct dyes remaining on the hair for as long as possible to deliver the desired hair color in the desired quality for as long as possible, according to the invention there are proposed compositions of the aforementioned kind in which the carrier system is vesicular and comprises vesicles which are made up from hydrophobised polysaccharides and have a particle size of between 10 and 1000 nm as well as a positive surface charge with a zeta potential in the range of between 1 and 150 mV.

15 Claims, No Drawings

COSMETIC COMPOSITION FOR COLORING HAIR COMPRISING A DIRECT HAIR DYE AND A CARRIER SYSTEM COMPRISING POLYSACCHARIDES

This application claims priority under 35 U.S.C. §119 and/or §365 to German Application No. 10 2010 030 000.4-43, filed on Jun. 11, 2010, the entire contents of which are incorporated herein by reference.

The present invention concerns a cosmetic composition for coloring hair comprising at least one direct hair dye encapsulated in a vesicular carrier system, and the use of such a composition in corresponding cosmetic formulations for coloring hair.

Many people want to have a hair color which is different from their natural one temporarily or permanently and there is a whole series of processes for imparting a different color to hair.

One of those processes involves using direct hair dyes which are attached to or incorporated in the cuticulas of the hair. That semi-permanent or temporary process therefore involves a coloring in which the naturally present pigment of the hair is not altered so that the new color shade is afforded together with the natural hair color. In contrast thereto there are also processes with hair dyes which chemically change the natural hair color by bonding for example chemically to certain amino acids in the hair.

Many direct hair dyes do not by nature adhere to or be incorporated in the cuticulas with the desired permanence and many do not penetrate into the cortex of the hair at all, for example because of their molecule size. Hair coloring agents with such hair dyes therefore often do not lead to coloring with the desired permanence. There is therefore a need for a possible way of prolonging the permanence of attachment or incorporation of direct hair dyes.

Therefore the object of the present invention is to provide a possible way with which the permanence of the bond of direct hair dyes to or in the hair can be improved. The aim is to provide that direct dyes remain on the hair as long as possible in order to afford the desired hair color of the desired quality for as long as possible.

According to the invention that object is attained by a cosmetic composition for coloring hair comprising at least one direct hair dye encapsulated in a vesicular carrier system, wherein the vesicular carrier system comprises vesicles which are made up from hydrophobised polysaccharides and have a particle size of between 10 and 1000 nm as well as a positive surface charge with a zeta potential in the range of between 1 and 150 mV.

By means of the carrier system of the composition according to the invention direct dyes thus provide the desired hair color of the desired quality for longer than without the carrier system of the composition according to the invention, which in fact is to be attributed to the fact that direct dyes by means of the carrier system of the composition according to the invention remain on the hair for longer.

Presumably the carrier system of the composition according to the invention provides that the permanence of direct hair dyes being attached to the hair is improved by the dye adhering more firmly to the hair to be attached there, in which respect however those observations are not intended to be binding in relation to the present invention and the scope of the invention is also not intended to be limited thereby.

In addition the composition according to the invention provides for better stabilisation of the hair dye, which leads to an increase in the amount of intact hair dye which is provided on the hair, which in turn has the effect that the desired hair color can be maintained for longer at the desired quality.

The term 'encapsulation' in connection with the present invention means embedding in principle of direct hair dyes between the polysaccharide molecules and the nanostructures afforded by the polysaccharide molecules as well as inclusion of the direct hair dyes in the vesicle interior.

The vesicles according to the invention have a zeta potential in the range of between 1 and 150 mV. The term 'zeta potential' describes the electrical potential of a slipping layer of a moved particle in a suspension. Measurement of the zeta potential can be effected by moving particles through an applied electrical field. The zeta potential can then be calculated from the resulting speed of the particles. In certain embodiments the vesicles have a zeta potential of between 30 and 100 mV. In certain lipid vesicles the zeta potential is between 40 and 60 mV.

The improved adhesion of the composition is based inter alia on the positive charge of the vesicle surface. The positive charge of the vesicle surface leads to improved adhesion of the vesicles to the surface of hair. It has also been found that that improved adhesion is also related to the nano-scale particle size, according to the invention, of the carrier vesicles, in which respect however all those observations are not intended to be binding in relation to the present invention and are therefore also not intended to limit the scope of the invention.

The particle size of the vesicles according to the invention is between 10 and 1000 nm. In certain embodiments the particle size is between 100 and 400 nm. In other embodiments it is between 100 and 350 nm or between 100 and 250 nm.

The term 'particle size' in connection with the present invention signifies the mean particle size. The mean particle size can be determined by photon correlation spectroscopy. Photon correlation spectroscopy—also referred to as dynamic light scatter—is an optical measurement method for determining the size distribution of vesicles and particles in fluids. The method utilises the scatter of laser light through the vesicles.

The combination according to the invention of the positive charge of the vesicle surface and the nano-scale particle size of the carrier vesicles provides that direct hair dyes contained in the vesicles remain on or in the hair more permanently.

Preferably the positive charge of the vesicle surface is caused by the vesicles, in addition to the polysaccharides from which the vesicles are made up, having positively charged molecules as charge generators, wherein said charge generators are selected from primary, secondary, tertiary and quaternary alkyl ammonium salts or combinations thereof. In that respect $C_{12}$-$C_{22}$ alkyl ammonium salts are particularly preferred.

Quite particularly preferred as charge generators in the present invention are quaternary $C_{12}$-$C_{22}$ alkyl trimethyl ammonium salts (or fatty acid trimonium salts) of the formula:

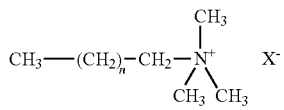

wherein n is an integer of between 10 and 22 and $X^-$ is an inorganic or organic anion. Preferably n in the above-specified alkyl trimethyl ammonium salt formula is equal to 22.

Preferably X⁻ in the above-specified formula is a halogenide ion or the anion of an organic acid selected from a cosmetically or pharmaceutically compatible carboxylic acid or sulfonic acid. Particularly preferably X⁻ is bromide, chloride, fluoride, iodide, saccharinate, tosylate or methosulfate.

Preferably the charge generators in the present invention are selected from one or more of ceteartrimonium chloride, cetrimonium bromide, cetrimonium chloride, cetrimonium saccharinate, cetrimonium tosylate, cocotrimonium chloride, cocotrimonium methosulfate, lautrimonium bromide, lautrimonium chloride, myrtrimonium bromide, octyldecyltrimonium chloride, steartrimonium bromide, steartrimonium chloride, steartrimonium methosulfate and steartrimonium saccharinate. In a particularly preferred embodiment of the present invention behentrimonium chloride is used as the charge generator.

Preferably in the present invention one or more of the aforementioned positively charged charge generators is used in such a way that the charge generator proportion in the vesicles with respect to the total weight of the vesicles is overall in the range of between 0.01 and 10% by weight. In certain embodiments the charge generator proportion is in the range of between 0.01 and 2.0% by weight.

The proportions specified in percent by weight relate in principle to the complete formulation of the hair coloring agent in accordance with formulation standards, inclusive of the proportion of water required for vesicle formation, unless something different is specified.

The specified proportion also includes all substances which clearly fall within the definition of the respective group of substances. Accordingly the specified charge generator proportion in the embodiments with one charge generator includes the proportion of that one charge generator and in embodiments having a plurality of charge generators it includes the total of all charge generators. That moreover applies in the same manner to proportions, specified in connection with this invention, of hydrophobised polysaccharide, filter substance and adjuvant or other substances or material proportions.

The basic polysaccharide structure of the hydrophobised polysaccharides which can be used in the hair coloring agent for formation of the vesicles can be selected from all cosmetically or pharmaceutically compatible polysaccharides which are capable of forming vesicles. Preferably this involves water-soluble polysaccharides and/or ethers thereof with short-chain alcohols ($C_1$ through $C_4$), wherein the water-soluble polysaccharides can be straight-chain, branched, comb-like and/or stellate. Straight-chain water-soluble polysaccharides are particularly preferred. Copolymers or block copolymers of different monosaccharide units and/or monosaccharide units which are linked together in different ways can also be considered.

The hydrophobised polysaccharides from which the vesicles are made up preferably have a basic polysaccharide structure of polyglucose or polyfructose. Preferred hydrophobised polysaccharides with a basic polysaccharide structure of a polyglucose are cellulose, methyl cellulose, hydroxyethyl cellulose, amylose, amylopectin and dextrin. A preferred hydrophobised polysaccharide with a basic polysaccharide structure of polyfructose is inulin.

In the present invention the hydrophobised polysaccharide preferably includes on average between 5 and 1000 monosaccharide units. Between 10 and 500 monosaccharide units are still more preferred. In certain embodiments between 20 and 100 monosaccharide units are preferred.

In especial embodiments it is also possible to use mixtures of the above-mentioned polysaccharides, with the proviso that those mixtures are capable of forming vesicles.

The proportion of the polysaccharides in the vesicles in relation to the total weight of the vesicles is in the range of between 1 and 85% by weight. Preferably the polysaccharide proportion in relation to the total weight of the vesicles is between 5 and 25% by weight. In certain embodiments the polysaccharide proportion is between 8 and 15% by weight.

In preferred embodiments the hydrophobised polysaccharides from which the vesicles are made up are hydrophobised by their having a basic polysaccharide structure with $C_{3-22}$ alkyl groups which are bonded by way of alkyl ether bonds or by way of alkyl urethane bonds to the hydroxy groups of the polysaccharide or which are bonded by way of a linker (for example polyether linker, polyethylene glycol linker) to the basic polysaccharide structure.

The molecular weight of the hydrophobically modified polysaccharide in preferred embodiments is in the range of between 5000 and 500,000 g/mol. In that respect the range of between 5000 and 100,000 g/mol is preferred.

In preferred hydrophobically modified polysaccharides the quotient of the number of hydrophobically modifying groups and modifiable groups (modification degree) is between 0.01 and 0.9. In particularly preferred embodiments the modification degree is between 0.03 and 0.15.

The hydrophobic groups and also the polysaccharide backbone can be substituted one or more times in certain embodiments by for example halogen, hydroxy, alkoxy, amino, alkyl amino, aryl, arylalkyl, carboxy, carboxyester and cycloaliphatic residues. Preferably the hydrophobically modified polysaccharides however involve non-ionic compounds.

In the present invention without limitation all water-soluble and fat-soluble hair dyes which are permitted at present and permitted in the future in accordance with the cosmetic regulations as well as any combinations of those dyes which can be encapsulated can be considered as the direct hair dyes. That can involve both lipophilic (oil-soluble) and also hydrophilic (water-soluble) dyes which were isolated from natural sources or produced chemically or biotechnologically, such as for example plant dyes such as henna or indigo, ioanilines, indophenoles, nitrobenzene derivatives, anthraquinone dyes, triphenylmethane dyes, quinone dyes, azo dyes, and cationic and anionic dyes.

Examples of direct hair dyes which can be used in the present invention are without limitation thereto:

TABLE 1 direct hair dyes

| Colipa No. | INCI | CAS No. | EINECS No. | Color Index No |
|---|---|---|---|---|
| B001 | Acid Yellow 1 | | | |
| B005 | Disperse Red 17 | 3179-89-3 | 221-665-5 | CI 11210 |
| B007 | Basic Brown 17 | 68391-32-2 | 269-944-0 | CI 12251 |

TABLE 1-continued direct hair dyes

| Colipa No. | INCI | CAS No. | EINECS No. | Color Index No |
|---|---|---|---|---|
| B024 | 4-NITRO-o-PHENYLENEDIAMINE | 99-56-9 | 202-766-3 | CI 76020 |
| B031 | HC RED NO. 13 | 29705-39-3 | 94158-13-1 | |
| B034 | N,N'-BIS(2-HYDROXYETHYL)-2-NITRO-p-PHENYLENEDIAMINE | 84041-77-0 | 281-856-4 | |
| B036 | HC RED NO. 7 | 24905-87-1 | 246-521-9 | |
| B037 | HC BLUE NO. 2 | 33229-34-4 | 251-410-3 | |
| B047 | HC ORANGE NO. 1 | 54381-08-7 | 259-132-4 | |
| B048 | HC RED NO. 1 | 2784-89-6 | 220-494-3 | |
| B051 | 4-AMINO-3-NITROPHENOL | 610-81-1 | 210-236-8 | |
| B052 | 2-HYDROXYETHYLAMINO-5-NITROANISOLE | 66095-81-6 | 266-138-0 | |
| B054 | 3-NITRO-p-HYDROXYETHYLAMINOPHENOL | 65235-31-6 | 265-648-0 | |
| B055 | 2-AMINO-3-NITROPHENOL | 603-85-0 | | |
| B056 | 6-NITRO-o-TOLUIDINE | 570-24-1 | 209-329-3 | |
| B058 | 3-METHYLAMINO-4-NITROPHENOXY-ETHANOL | 59820-63-2 | 261-940-7 | |
| B060 | 2-NITRO-5-GLYCERYL METHYLANILINE | 80062-31-3 | 279-383-3 | |
| B063 | HC YELLOW NO. 11 | 73388-54-2 | — | |
| B066 | HC VIOLET NO. 1 | 82576-75-8 | 417-600-7 | |
| B067 | HC ORANGE NO. 2 | 85765-48-6 | 416-410-1 | |
| B069 | HC YELLOW NO. 9 | 141973-33-3 | 86419-69-4 | |
| B070 | 4-NITROPHENYL AMINOETHYLUREA | 27080-42-8 | 410-700-1 | |
| B071 | HC RED NO. 10 AND HC RED NO. 11 | 95576-89-9 + 95576-92-4 | 408-240-1 | |
| B072 | 2-HYDROXYETHYL PICRAMIC ACID | 99610-72-7 | 412-520-9 | |
| B073 | HC BLUE NO. 12 | 132885-85-9 | 407-020-2 | |
| B075 | HYDROXYETHYL-2-NITRO-P-TOLUIDINE | 100418-33-5 | 408-090-7 (ELINCS) | |
| B077 | HC BLUE NO. 11 | 23920-15-2 | 459-980-7 | |
| B080 | HC YELLOW NO. 7 | 104226-21-3 | | |
| B087 | 4-AMINO-2-NITROPHENYL-AMINE-2'-CARBOXYLIC ACID | 117907-43-4 | — | |
| B089 | 2-CHLORO-6-ETHYLAMINO-4-NITROPHENOL | 131657-78-8 | 411-440-1 | |
| B098 | HC VIOLET NO. 2 | | | |
| B099 | 2-Amino-6-Chloro-4-Nitrophenol | 6358-09-4 | 228-762-1 | |
| B100 | 4-Hydroxypropylamino-3-Nitrophenol | 92952-81-3 | 406-305-9 | |
| B102 | HC YELLOW NO. 13 | 10442-83-8 | | |
| B104 | 1,2,3,4-TETRAHYDRO-6-NITROCHINOXALIN | 158006-54-3 (hydrochloride) | — | |
| B113 | Basic Orange No. 69 | 226940-14-3 | — | CI 112605 |
| B115 | Basic Violet 2 | 3248-91-7 | 221-831-7 | CI 42520 |
| C008 | Basic Red 76 | 68391-30-0 | 269-941-4 | CI 12245 |
| C009 | Basic Brown 16 | 26381-41-9 | 247-640-9 | CI 12250 |
| C010 | Basic Yellow 57 | 68391-31-1 | 269-943-5 | CI 12719 |
| C015 | Orange 4 | 633-96-5 | 211-199-0 | CI 15510 |
| C022 | Red 33 | 3567-66-6 | 222-656-9 | CI 17200 |
| C029 | Yellow 5 - Acid Yellow 23 | 1934-21-0 | 217-699-5 | CI 19140 |
| C040 | Acid Blue 9 - Blue 1 | 3844-45-9 | 4223-333-98 | CI 42090 |
| C046 | Basic Blue 7 | 2390-60-5 | | CI 42595 |
| C053 | Acid Red 92 | 18472-87-2 | 242-355-6 | CI 45410 |
| C054 | Yellow 10 - Acid Yellow 3 | — | — | CI 47005 |
| C059 | Basic Blue 99 | 68123-13-7 | — | CI 56059 |
| C063 | Acid Violet 43 - Ext. Violet 2 | 4430-18-6 | 224-618-7 | CI 60730 |
| C064 | Disperse Violet 1 | 128-95-0 + 116-85-8 | — | |
| C067 | ACID BLUE 62 | 4368-56-3 | 224-460-9 | CI 62045 |
| C117 | HYDROXYANTHRAQUINONEAMINOPROPYLMETHYL MORPHOLINIUM METHOSULFATE | 38866-20-5 | 254-161-9 | |
| C119 | HC RED NO. 8 | 13556-29-1 | 306-778-0 | |
| C129 | HC GREEN NO. 1 | 52136-25-1 | 257-687-7 | |
| C146 | LAWSONE | 83-72-7 | — | CI 75480 |
| C169 | Henna (Lawsonia inermis) | 84988-66-9 | — | |
| C172 | HC BLUE No. 14 | 99788-75-7 | — | |
| C174 | CURRY RED | 25956-17-6 | 247-368-0 | CI 16035 |

TABLE 1-continued direct hair dyes

| Colipa No. | INCI | CAS No. | EINECS No. | Color Index No |
|---|---|---|---|---|
| C175 | Acid Red 18 | 2611-82-7 | 220-036-2 | CI 16255 |
| C177 | Acid Red 52 | 3520-42-1 | 222-529-8 | CI 45100 |
| C178 | Acid Green 25 | 4403-90-1 | 224-546-6 | CI 61570 |

Preferably the proportion of direct hair dye in the present invention is between 0.01 and 40% by weight with respect to the overall composition.

In certain embodiments there are combinations of two or more direct hair dyes, wherein the sum of those dyes makes up between 0.01 and 40% by weight with respect to the overall composition.

In certain embodiments the composition according to the invention additionally has at least one UV filter substance having a chemical or physical UV filter effect.

In this respect all substances having a chemically or physically UV filtering action are unlimitedly considered as the UV filter substance, provided they are soluble in oil. The chemical filter substances absorb high-energy radiation and discharge it again as lesser-energy, longer-wave radiation or heat. The physical filter substances primarily scatter and reflect the light.

Preferred examples of UV filter substances which can be used in the present invention and without limitation thereto are 3-benzylidene campher, 4-methylbenzylidene campher, benzophenone-1, benzophenone-2, benzophenone-3, benzophenone-4, benzophenone-5, benzophenone-6, benzophenone-9, benzylidene campher sulfonic acid, bis-ethyl hexyloxyphenol methoxyphenyl triazine, butylmethoxydibenzoyl methane, campherbenzalkonium methosulfate, diethylaminohydroxybenzoylhexyl benzoate, diethylhexylbutamidotriazone, dinatriumphenyldibenzimidazole tetrasulfonate, drometrizoltrisiloxane, ethylhexyldimethylpaba, ethylhexylmethoxy cinnamate, ethyl hexyl salicylate, ethylhexyltriazone, homosalate, isoamyl-p-methoxy cinnamate, methylenebis-benzotriazolyl tetramethylbutylphenol, octocrylene, PEG-25-Paba, phenylbenzimidazol sulfonic acid, polyacrylamidomethyl benzylidene campher, polysilicone-15, potassium phenylbenzimidazol sulfonate, sodium mangoseedate, sodium phenylbenzimidazole sulfonate, tea-phenylbenzimidazole sulfonate, terephthalylidene dicampher sulfonic acid, ferulic acid, cinoxate, diisopropylmethyl cinnamate, 4-(2-beta-glucopyranosiloxy)propoxy-2-hydroxybenzophenone, glycerylethylhexanoate dimethoxy cinnamate, and isopentyltrimethoxy cinnamate trisiloxane.

Preferably the proportion of UV filter substance in the present invention is between 1 and 65% by weight with respect to the total weight of the complete formulation of the hair coloring agent in accordance with composition standards, inclusive of the proportion of water required for vesicle formation.

As generally the individual filter substances do not afford any protection over the entire UV spectrum in preferred embodiments of the invention a plurality of filter substances are combined to achieve UV protection which is as broad as possible.

The composition according to the invention can also contain all adjuvants and additives which are usually employed in cosmetic preparations. In particular the term 'adjuvant' in connection with the present invention includes such additives which act on the physical properties of the vesicles and the stability thereof and/or serve for preservation of the hair coloring agents. Examples of such adjuvants are oils, alcohols, polyols, antioxidants, gel-forming agents, buffers, preserving agents, bactericides and germ inhibitors, consistency agents, thickeners or complexing agents.

Preferably the composition according to the invention is characterised in that the adjuvant proportion with respect to the total weight of the complete formulation of the hair coloring agent in accordance with composition standards, inclusive of the proportion of water required for vesicle formation, is in the range of between 0.01 and 10% by weight.

According to the invention the composition for coloring hair is preferably used in cosmetic formulations for coloring hair. In that case the composition according to the invention can be present in all formulations suitable for coloring hair, for example in the form of a coloring shampoo or coloring styling mousse or in the form of toning lotions, color mousses or toning mousse.

The proportion of dyes in the overall formulation is preferably between 0.001 and 10%.

It will be appreciated that all components of the compositions and formulations according to the invention are cosmetically compatible substances. A substance is cosmetically compatible in accordance with this invention if it is non-toxic and can be used in regard to the majority of potential users without the user suffering spontaneously or after a while an unwanted physiological reaction such as for example skin reddening or itching.

For the purposes of the original disclosure it is pointed out that all features as can be seen by a man skilled in the art from the present description and the claims, even if they are described in specific terms only in connection with certain other features, can be combined both individually and also in any combinations with others of the features or groups of features disclosed here insofar as that has not been expressly excluded or chemical, physical-chemical, cosmetic, pharmacological or dermatological aspects make such combinations impossible or meaningless. A comprehensive explicit representation of all conceivable combinations of features is dispensed with here only for the sake of brevity and readability of the description.

The invention claimed is:

1. A cosmetic composition for coloring hair comprising at least one direct hair dye encapsulated in a vesicular carrier system, wherein the vesicular carrier system comprises vesicles which are made up from hydrophobised polysaccharides and have a particle size of between 10 and 1000 nm as well as a positive surface charge with a zeta potential in the range of between 1 and 150 mV.

2. A composition according to claim 1 wherein the hair dye proportion in the vesicles with respect to the total weight of the composition is in the range of between 1 and 65% by weight.

3. A composition according to claim 2 wherein the polysaccharide proportion in the vesicles with respect to the total weight of the vesicles is in the range of between 1 and 85% by weight.

4. A composition according to claim 1 wherein the positive surface charge is caused by the vesicles in addition to the polysaccharides from which the vesicles are made up having positively charged molecules as charge carriers, wherein said charge carriers are selected from primary, secondary, tertiary and quaternary alkyl ammonium salts or combinations thereof.

5. A composition according to claim 4 wherein the charge generator proportion in the vesicles with respect to the total weight of the composition is in the range of between 0.01 and 10% by weight.

6. A composition according to claim 1 wherein the hydrophobised polysaccharides from which the vesicles are made up have a basic polysaccharide structure of polyglucose or polyfructose.

7. A composition according to claim 1 wherein the hydrophobised polysaccharides from which the vesicles are made up have a basic polysaccharide structure of polyglucose selected from cellulose, methyl cellulose, hydroxyethyl cellulose, amylose, amylopectin or dextrin, or have a basic polysaccharide structure of the polyfructose inulin.

8. A composition according to claim 1 wherein the hydrophobised polysaccharides from which the vesicles are made up have a basic polysaccharide structure hydrophobically modified by $C_{3-22}$ alkyl groups which are bonded by way of alkyl ether bonds or by way of alkyl urethane bonds to the hydroxy groups of the polysaccharide or which are bonded to the basic polysaccharide structure by way of a linker.

9. A composition according to claim 1 wherein it additionally has at least one UV filter substance having a chemical or physical UV filter action.

10. A composition according to claim 9 wherein the at least one UV filter substance is selected from 3-benzylidene campher, 4-methylbenzylidene campher, benzophenone-1, benzophenone-2, benzophenone-3, benzophenone-4, benzophenone-5, benzophenone-6, benzophenone-9, benzylidene campher sulfonic acid, bis-ethylhexyloxyphenol methoxyphenyl triazine, butylmethoxydibenzoyl methane, campherbenzalkonium methosulfate, diethylaminohydroxybenzoylhexyl benzoate, diethylhexylbutamidotriazone, dinatriumphenyldibenzimidazole tetrasulfonate, drometrizoltrisiloxane, ethylhexyldimethylpaba, ethylhexylmethoxy cinnamate, ethylhexyl salicylate, ethylhexyltriazone, homosalate, isoamyl-p-methoxy cinnamate, methylene-bis-benzotriazolyl tetramethylbutylphenol, octocrylene, PEG-25-Paba, phenylbenzimidazol sulfonic acid, polyacrylamidomethyl benzylidene campher, polysilicone-15, potassium phenylbenzimidazol sulfonate, sodium mangoseedate, sodium phenylbenzimidazole sulfonate, tea-phenylbenzimidazole sulfonate, terephthalylidene dicampher sulfonic acid, ferulic acid, cinoxate, diisopropylmethyl cinnamate, 4-(2-beta-glucopyranosiloxy)propoxy-2-hydroxybenzophenone, glycerylethylhexanoate dimethoxy cinnamate, and isopentyltrimethoxy cinnamate trisiloxane.

11. A composition according to claim 1 including one or more adjuvants.

12. A composition according to claim 1 wherein the adjuvant proportion in the vesicles with respect to the total weight of the composition is in the range of between 0.01 and 10% by weight.

13. A method of coloring hair comprising applying to the hair a composition according to claim 1.

14. A cosmetic formulation comprising a composition according to claim 1.

15. The method according to claim 13 wherein the dye proportion in the composition with respect to the total weight thereof is in the range of between 0.001 and 10% by weight.

* * * * *